US00PP27064P3

(12) United States Plant Patent
Zaiger et al.

(10) Patent No.: US PP27,064 P3
(45) Date of Patent: Aug. 16, 2016

(54) INTERSPECIFIC TREE NAMED 'BELLA BABY'

(50) Latin Name: **Interspecific *Prunus* species**
Varietal Denomination: Bella Baby

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 91 days.

(21) Appl. No.: 14/544,285

(22) Filed: Dec. 22, 2014

(65) Prior Publication Data

US 2016/0183421 P1 Jun. 23, 2016

(51) Int. Cl.
*A01H 5/08* (2006.01)

(52) U.S. Cl.
USPC ..... Plt./180

(58) Field of Classification Search
USPC ..... Plt./180
See application file for complete search history.

*Primary Examiner* — Susan McCormick Ewoldt

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree with a vigorous, upright growth.
2. Tree being a regular and productive bearer of small to medium size fruit.
3. Fruit with excellent flavor and eating quality.
4. Fruit with an attractive red skin color.
5. Fruit with good storage and shipping qualities.

1 Drawing Sheet

Botanical designation: Interspecific *Prunus* species.
Variety denomination: 'Bella Baby'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of interspecific trees, which are known to us, and mentioned herein, 'Bella Sun' Interspecific (U.S. Plant Pat. No. 21,817) and our proprietary non-patented interspecific seedling selections '32MD466', '29ZK170', '6ZB206', '10HD820', '122LE654' and '11M130'.

STATEMENT REGARDING FEDERALLY SPONSORED RESEARCH AND DEVELOPMENT

Not applicable.

ORIGIN OF THE VARIETY

The new and distinct variety of interspecific tree consists of crosses between the following species; *Prunus salicina* and

*Prunus armeniaca*. It was originated by us in our experimental orchard located near Modesto, Calif. as a first generation cross between our proprietary non-patented interspecific seedling selections with the field identification numbers '32MD466' and '29ZK170'. The non-patented interspecific seed parent (32MD466) originated from crosses between our proprietary non-patented interspecific seedling selections '6ZB206' and '10HD820'. The non-patented interspecific pollen parent (29ZK170) originated from crosses between our proprietary non-patented interspecific seedling selections '122LE654' and '11M130'. A large number of these first generation seedlings were budded onto older established trees of 'Nemaguard' Rootstock (non-patented) to enhance earlier fruit production. Under close and careful observation the present seedling exhibited desirable fruit and tree characteristics and was selected in 2011 for additional asexual propagation and commercialization.

ASEXUAL REPRODUCTION OF THE VARIETY

In 2011 asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new and distinct variety of interspecific tree is of large size, vigorous, upright growth and a regular and productive bearer of small to medium size, red flesh, clingstone fruit with excellent flavor and eating quality. The fruit is further characterized by having an attractive red skin color and having good handling and shipping qualities. In comparison to its non-patented interspecific seed parent '32MD466' the fruit of the new variety has red flesh compared to yellow pink and ripens approximately 7 days later in maturity. In comparison to its non-patented interspecific pollen parent '29ZK170' the fruit of the new variety has red flesh compared to yellow and is approximately 17 days later in maturity. In comparison to the commercial variety 'Bella Sun' Interspecific (U.S. Plant Pat. No. 21,817) the fruit of the new variety has an attractive red skin color compared to yellow orange and has red flesh compared to yellow.

DESCRIPTION OF THE PHOTOGRAPH

The accompanying color photographic illustration shows typical specimens of the foliage and fruit of the present new interspecific variety.

The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 5 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 5 year old specimens grown near Modesto, Calif., with color in accordance with Munsell Book of Color published in 1958.

Tree:

*Size*.—Large, usually pruned to 3 to 3.5 meters in height and width for economical harvesting of fruit. Size can vary with different cultural practices.

*Vigor*.—Vigorous, growth of 1.5 to 2 meters the first growing season. Varies slightly with soil type, fertility of soil and climatic conditions.

*Form*.—Upright, usually pruned to vase shape.

*Branching habit*.—Upright, crotch angle approximately. 35°, increases with heavy crop load.

*Productivity*.—Productive, thinning and spacing of fruit necessary for desired marketable size. Fruit set varies with climatic conditions during bloom time.

*Bearer*.—Regular, has had adequate fruit set 3 consecutive years. No alternate bearing observed.

*Fertility*.—Self sterile, pollinator required.

*Density*.—Medium dense, pruning to vase shape desirable for sunlight penetration to center of tree to enhance fruit color and health of fruit spurs.

*Hardiness*.—Hardy in all stone fruit growing areas of California. Tree grown in USDA Hardiness Zone 9. Winter chilling requirement approximately 600 hours at or below 45° F.

Trunk:

*Size*.—Large. Average circumference 40.5 cm at 25.4 cm above ground on a 5 year old tree.

*Stocky*.—Medium stocky.

*Texture*.—Medium shaggy, roughness increases with age.

*Color*.—Varies from 5Y 3/2 to 7.5Y 5/2.

Branches:

*Size*.—Medium. Average circumference 13.0 cm at 1.2 meters above ground. Crotch angle approximately 35°, increases with heavy crop load.

*Surface texture*.—New growth relatively smooth. Mature growth medium rough, roughness increases with age.

*Lenticels*.—Average number 32 in a 25.8 square cm section. Average length 3.8 mm. Average width 1.4 mm. Color varies from 10YR 6/10 to 2.5Y 6/4.

*Color*.—New growth varies from 5GY 6/8 to 2.5YR 6/4. Mature growth varies from 5YR 2/2 to 7.5YR 6/2, varies with age of growth.

Leaves:

*Size*.—Medium to large. Average length 88.3 mm. Average width 68.7 mm.

*Form*.—Globose to oblanceolate.

*Apex*.—Acuminate.

*Base*.—Obtuse.

*Margin*.—Doubly serrate.

*Thickness*.—Medium.

*Surface texture*.—Upper surface relatively smooth, slight indentations over midrib and leaf veins. Lower surface relatively smooth, except for small ridges created by midrib and pinnate venation. Both upper and lower surfaces glabrous.

*Petiole*.—Average length 18.5 mm. Average width 1.6 mm. Longitudinally grooved. Surface — light pubescence. Color varies from 2.5GY 7/6 to 7.5R 4/6.

*Glands*.—Type — globose. Size — small to medium. Average length 1.0 mm. Average diameter 0.7 mm. Number varies from 2 to 4, average number 3. Located primarily on upper portion of petiole and base of leaf blade. Color varies from 2.5GY 5/8 to 2.5GY 5/6.

*Stipules*.—Average number 2. Average length 6.6 mm. Edges — pectinate. Color varies from 10Y 7/6 to 2.5GY 8/6.

*Color*.—Upper surface varies from 5GY 4/6 to 5GY 3/6. Lower surface varies from 5GY 5/4 to 5GY 4/4. Midvein color varies from 2.5GY 7/6 to 2.5GY 6/6.

Flower buds:

*Size*.—Large. Average length 10.1 mm. Average diameter 7.5 mm.

*Hardiness*.—Hardy with respect to California winters.

*Density*.—Medium dense.

*Form*.—Conical, becoming elongated just before opening.

*Pedicel*.—Average length 1.7 mm. Average width 1.1 mm. Color varies from 2.5GY 6/6 to 5GY 7/6. Surface — glabrous.

*Color*.—N 9.5/ (white).

*Number of buds per spur*.—Average 5, varies from 4 to 8. Varies with age of spur.

Flowers:

*Blooming period*.—Date of First Bloom Feb. 7, 2014. Date of Petal Fall Feb. 17, 2014, varies slightly with climatic conditions.

*Size*.—Medium to large. Average height 10.6 mm. Average diameter 31.3 mm.

*Petals*.—Normally 5, alternately arranged to sepals. Size. — large. Average length 16.2 mm. Average width 13.6 mm. Petal apex — rounded. Petal base — rounded to somewhat truncated. Form — obovate. Arrangement — free to overlapping. Margin — sinuate. Color N 9.5/ (white).

*Sepals*.—Normally 5, alternately arranged to petals. Size — medium. Average length 4.4 mm. Average width 3.9 mm. Shape — triangular. Apex rounded to triangular. Margin — entire. Both upper and lower surfaces glabrous. Color — upper surface varies from 5GY 8/4 to 5RP 4/10. Lower surface varies from 5R 4/10 to 5R 4/12.

*Stamens*.—Average number per flower 31. Average filament length 7.0 mm. On average the stamens are below the height of the petals. Filament color N 9.5/ (white). Anther color varies from 5Y 8.5/8 to 5Y 8/8.

*Pollen*.—Self sterile, pollinator required. Color varies from 5Y 7/10 to 5Y 7/12.

*Pistil*.—Number — normally one. Average length 11.0 mm. Position of stigma an average of 1.8 mm below anthers. Surface — pubescent. Color varies from 10Y 8.5/4 to 10Y 8/6.

*Fragrance*.—Heavy aroma.

*Color*.—N 9.5/ (white).

*Pedicel*.—Average length 2.2 mm. Average width 1.1 mm. Color varies from 2.5GY 6/6 to 5GY 7/6.

*Number flowers per flower bud*.—Average 2, varies from 1 to 3.

Fruit:

*Maturity when described*.—Firm ripe and ready for consumption.

*Date of first picking*.—May 30, 2014.

*Date of last picking*.—Jun. 9, 2014, varies slightly with climatic conditions.

*Size*.—Small to medium. Average diameter axially 52.2 mm. Average transversely in suture plane 60.8 mm. Average weight 130.6 grams, varies slightly with fertility of the soil, amount of thinning and climatic conditions.

*Form*.—Globose.

*Suture*.—Slightly lipped.

*Ventral surface*.—Slightly lipped to nearly smooth.

*Apex*.—Slightly retuse.

*Base*.—Retuse.

*Stem cavity*.—Rounded to slightly elongated in suture plane. Average depth 4.7 mm. Average diameter 5.5 mm.

Stem:

*Size*.—Small. Average length 6.4 mm. Average diameter 2.6 mm.

*Color*.—Varies from 10Y 6/8 to 10Y 5/8.

Flesh:

*Ripens*.—Evenly.

*Texture*.—Firm, meaty.

*Fibers*.—Few, small, tender.

*Firmness*.—Firm, comparable to other interspecific varieties.

*Aroma*.—Slight.

*Amydgalin*.—Undetected.

*Eating quality*.—Very good.

*Flavor*.—Very good with a good balance between acid and sugar.

*Juice*.—Heavy amount, enhances flavor.

*Acidity*.—Not available.

*Brix*.—Average Brix 15.2°, varies slightly with amount of fruit per tree and climatic conditions.

*Pit cavity*.—Average length 26.6 mm. Average width 22.6 mm. Average depth 7.0 mm. Color varies from 7.5R 3/8 to 7.5R 3/12.

*Color*.—Varies from 5R 5/12 to 5R 3/10.

Skin:

*Thickness*.—Medium.

*Surface*.—Smooth.

*Pubescence*.—Moderate amount, very short.

*Tendency to crack*.—None.

*Color*.—Ground color varies from 2.5Y 8.5/6 to 5Y 8/4. Overspread with 7.5R 4/10 to 7.5R 2/8.

*Tenacity*.—Tenacious to flesh.

*Astringency*.—Undetected.

Stone:

*Type*.—Clingstone, strong adherence.

*Size*.—Medium to large. Average length 25.6 mm. Average width 21.6 mm. Average thickness 11.9 mm.

*Form*.—Ovoid.

*Base*.—Flat.

*Apex*.—Pointed. Average length 1.7 mm.

*Surface*.—Slightly pitted throughout. One shallow groove on each side of suture extending from base toward apex.

*Sides*.—Unequal, one side extending further outward from suture plane.

*Ridges*.—Very narrow, small ridge near groove on each side of suture.

*Tendency to split*.—None.

*Color*.—Varies from 5YR 4/8 to 7.5YR 5/8 when dry.

Kernel:

*Size*.—Medium. Average length 15.7 mm. Average width 12.8 mm. Average depth 6.4 mm.

*Form*.—Ovate.

*Viability*.—Viable, complete embryo development.

*Skin color*.—Varies from 7.5Y 9/2 to 10Y 9/2.

Use: Dessert.

*Market*.—Local and long distance.

Keeping quality: Good, held firm in cold storage 3 weeks at 38° to 42° F. without shriveling, internal breakdown of flesh or appreciable loss of flavor.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program. No atypical resistances/susceptibilities have been noted under normal cultural practices. The present new variety of interspecific, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree, substantially as illustrated and described.

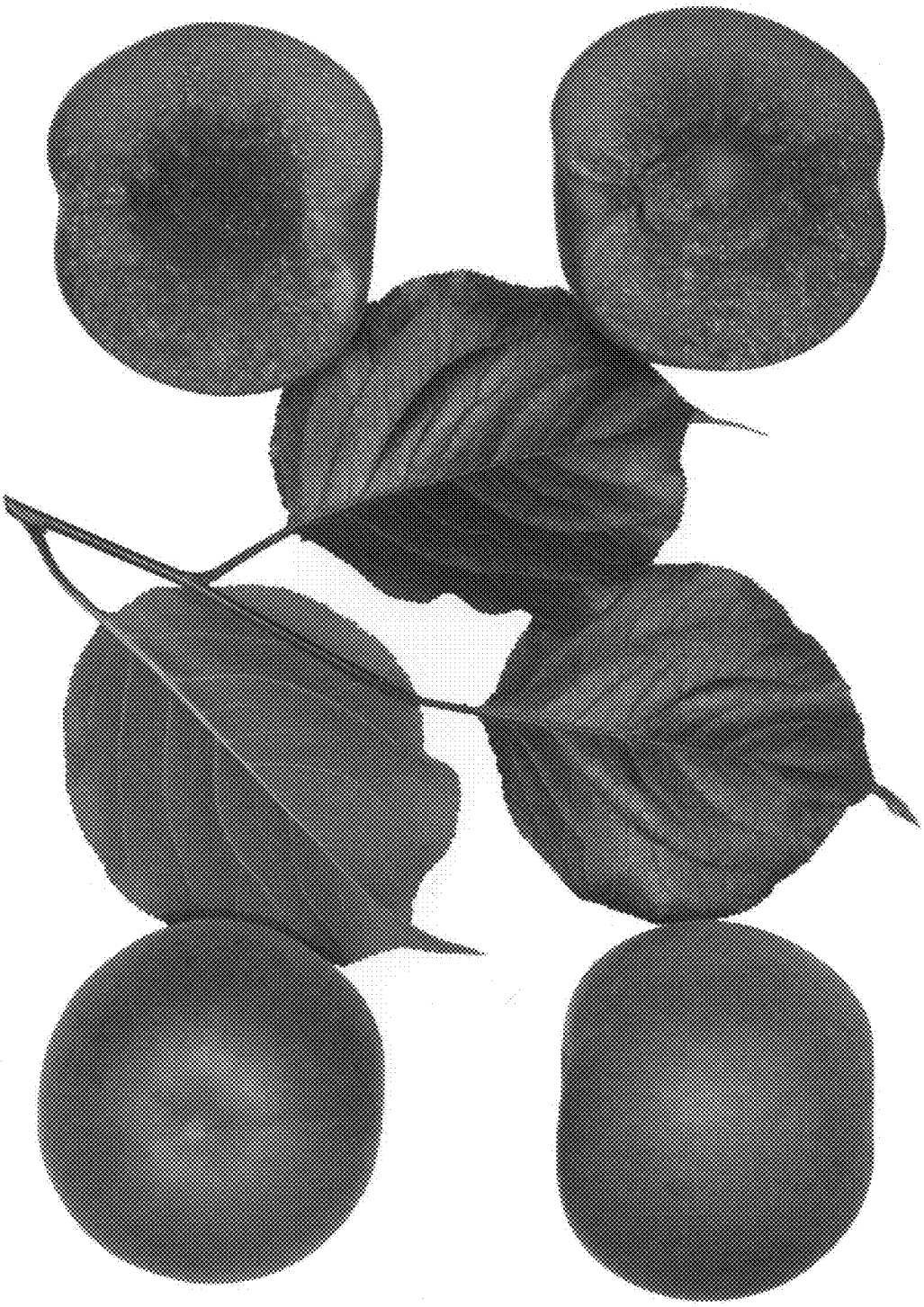

* * * * *